United States Patent

Inamoto et al.

[11] 4,086,285
[45] Apr. 25, 1978

[54] TRICYCLO[6.2.1.0$^{2,6}$]UNDECA-2(6)-ENE AND PROCESS FOR HYDRIDE TRANSFER REDUCTION REARRANGEMENT OF SAME

[75] Inventors: Yoshiaki Inamoto, Wakayama; Kiyoshi Tsuchihashi, Kainan; Naotake Takaishi, Wakayama; Yoshiaki Fujikura, Wakayama; Koji Aigami, Wakayama, all of Japan

[73] Assignee: Kao Soap Co., Ltd., Tokyo, Japan

[21] Appl. No.: 734,365

[22] Filed: Oct. 20, 1976

[30] Foreign Application Priority Data

Nov. 7, 1975 Japan .................. 50-133894

[51] Int. Cl.$^2$ ............................................. C07C 13/28
[52] U.S. Cl. ...................... 260/666 PY; 260/666 M
[58] Field of Search ................ 260/666 PY, 666 M

[56] References Cited

PUBLICATIONS

Naotake Takaishi et al., Chemical Abstracts, vol. 84: 10478j, 1976, [J. Org. Chem., 1976, 41 (5), 771–775].
Naotake Takaishi et al., J. Org. Chem., vol. 40, No. 3, 276–281, 1975.
Naotake Takaishi et al., J. Org. Chem., vol. 40, No. 10, 1483–1487, 1975.

*Primary Examiner*—Veronica O'Keefe
*Attorney, Agent, or Firm*—Blanchard, Flynn, Thiel, Boutell & Tanis

[57] ABSTRACT

Tricyclo[6.2.1.0$^{2,6}$]undeca-2(6)-ene is disclosed and there is further disclosed a process for the hydride transfer reduction rearrangement of tricyclo[6.2.1.0$^{2,6}$]undeca-2(6)-ene having the formula (I):

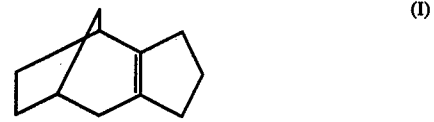

(I)

by subjecting tricyclo[6.2.1.0$^{2,6}$]undeca-2(6)-ene having the formula (I) to rearrangement with concentrated sulfuric acid in the presence of a hydride source to convert it to 4-homoisotwistane (tricyclo[5.3.1.0$^{3,8}$]undecane) having the formula (II):

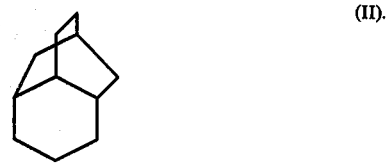

(II).

2 Claims, No Drawings

TRICYCLO[6.2.1.0²,⁶]UNDECA-2(6)-ENE AND PROCESS FOR HYDRIDE TRANSFER REDUCTION REARRANGEMENT OF SAME

BACKGROUND OF THE INVENTION

1. Field of the Invention

The present invention relates to tricyclo[6.2.1.0²,⁶]undeca-2(6)-ene and a process for the hydride transfer reduction rearrangement thereof.

Tricyclo[6.2.1.0²,⁶]undeca-2(6)-ene is a novel compound. Moreover the invention relates to a process for the synthesis of 4-homoisotwistane (tricyclo[5.3.1.0³,⁸]undecane), a known useful compound, having the formula (II):

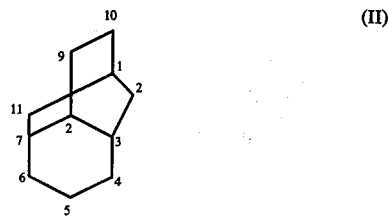

which comprises isomerizing tricyclo[6.2.1.0²,⁶]undeca-2(6)-ene having the formula (I):

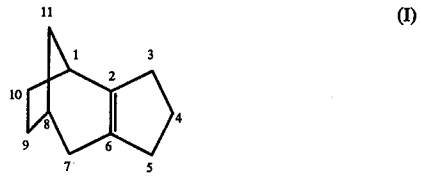

with concentrated sulfuric acid in the presence of a hydride source and simultaneously performing reduction with a hydride.

4-Homoisotwistane (II) is a compound recently synthesized for the first time by Krantz (Krantz, Chem. Commun., 1287 (1971) and J. Amer. Chem. Soc., 95, 5662 (1973)). It is a tricycloundecane having the same skeleton as that of seychellene, a kind of sesquiterpene.

We previously studied various functional reactions of the compound (II) and found that one of the derivatives of the compound (II), 3-amino-4-homoisotwistane, is a very effective antiviral agent.

The desired compound of formula (II) is very valuable as a starting compound for production of human medicines and animal medicines.

The process of the present invention can be performed very easily. Namely, the desired compound of formula (II) can be obtained by agitating the starting olefin of formula (I) at room temperature together with concentrated sulfuric acid and a hydrocarbon as a hydride source. After completion of the reaction, the hydrocarbon layer is separated and the hydrocarbon is removed by distillation or the like. Thus, the crude compound of formula (II) can be obtained in a yield of 35 to 40%, and the selectivity to the compound of formula (II) is as high as 92%. In acid-catalyzed isomerizations of tricycloundecanes, in general, if the reaction is not conducted until the final methyladamantane is formed and the reaction is stopped partway to completion, it seldom happens that a single product is predominantly obtained, but rather a complicated mixture of a number of tricycloundecane isomers is usually obtained (refer to our reports in J. Org. Chem., 40, 276 (1975), ibid, 1483 (1975), ibid, 40, 2929 (1975)). In view of the foregoing, it is quite surprising that in the process of the present invention, the compound of formula (II) can be obtained at such a high selectivity as 92%. This means that the process of the present invention is very valuable as a process for the synthesis of the compound of formula (II).

The concentrated sulfuric acid that is used in the process of the present invention has a concentration of 75 to 100%, preferably 90 to 98%. When the concentration is lower than 75%, isomerization is not advanced effectively, and when sulfuric acid having a concentration higher than 100% (fuming sulfuric acid) is used, an oxidation reaction takes place simultaneously and the yield is reduced. The amount of sulfuric acid employed is 1 to 1000 times, preferably 10 to 100 times, the amount of the starting formula (I) olefin (on a weight basis).

Any aliphatic or alicyclic hydrocarbon which has a boiling point in the range between 20° and 160° C, preferably 30° and 100° C, and is liquid under the reaction conditions can be effectively used as the hydrogen anion source. However, the use of hydrocarbons having an excessively high boiling point, such as above about 160° C, must be avoided, because separation of the intended product by distilling off the hydrocarbon becomes difficult. For example, as acceptable hydride sources there can be mentioned n-pentane, n-hexane, n-heptane, n-octane, cyclopentane, cyclohexane, cyclooctane, methylcyclohexane, isooctane, petroleum ether and ligroin. The amount used of the hydride source has no substantial influence on the yield of the desired compound of formula (II), but it is generally preferred to use the hydride source in an amount of from 10 to 10³ times the amount of the starting formula (I) olefin (on a weight basis).

The reaction temperature is in the range of from −20° to +100° C, and temperatures approximating room temperature (20° to 30° C) are especially preferred.

The starting compound of formula (I), tricyclo[6.2.1.0²,⁶]undeca-2(6)-ene, can be synthesized by dehydration isomerization of 5,6-exo-trimethylene-2-norbornylcarbinol (IV), 2-hydroxy-6,7-exo-trimethylenebicyclo[3.2.1]octane (V), 3-endo-hydroxy-6,7-exo-trimethylenebicyclo[3.2.1]octane (VI) or 2-hydroxy-5,6-endo-trimethylenebicyclo[2.2.2]octane (VII), in the presence of phosphoric acid, or by isomerization of 6,7-exo-trimethylenebicyclo[3.2.1]oct-2-ene (VIII), in the presence of phosphoric acid.

The starting carbinol (IV) is simply heated together with an excess amount of phosphoric acid. It is preferable to use a solvent in order to more intimately mix the carbinol (IV) with phosphoric acid. The solvent serves to suppress formation of polymer and thereby to increase the yield of the desired tricycloundecane.

The concentration of the used phosphoric acid may be 50 to 100%, preferably 70 to 90%. When a dilute phosphoric acid, i.e. the concentration thereof is less than 50%, is used, the dehydration reaction does not eventually take place. On the other hand, a phosphoric acid having a concentration of more than 100% promotes formation of polymers. The amount of phosphoric acid to be added may be 0.1 to 1000 times of the amount of the starting carbinol (IV), preferably 1 to 100 times. When the amount of the added phosphoric acid is less than 0.1 times the amount of the carbinol, the reaction speed is extremely retarded.

Any solvents which are inactive to phosphoric acid and the compounds (IV) and (I) may be used in this synthesis, the most suitable solvents being aliphatic hydrocarbons which have no tertiary hydrogen atom, alicyclic hydrocarbons and aromatic hydrocarbons. A solvent having a tertiary hydrogen atom should not be used, because such a solvent delays the desired reaction or occasionally prevents the reaction substantially. It is considered that the tertiary hydrogen atoms readily form hydrogen anions which tend to be transferred to carbocation from the carbinol (IV) or intermediate cations which are generated by isomerization of the carbocations thereby to retard or stop the isomerization reaction. Examples of usable solvents include n-pentane, n-hexane, n-heptane, cyclopentane, cyclohexane, benzene and toluene. The amount of the used solvent is not strictly restricted. However, the convenient amount of the used solvent is 1 to 1000 times, preferably 10 to 100 times, by weight of the amount of the starting carbinol (IV).

The reaction temperature may be 50° to 150° C, preferably 80° to 110° C.

5,6-Exo-trimethylene-2-norbonylcarbinol (IV) may be synthesized from 2-exo-chloro-5,6-exo-trimethylenenorbonane through a Grignard reaction or addition reaction to formaldehyde (Reference should be made to Japanese Patent Application No. 1974-62232 or Synth. Commun., 5 (1975) both by the inventors).

The compound (V) may be, for instance, synthesized by hydrolyzing 3,4-dichloro-6,7-exo-trimethylenebicyclo[3.2.1]octo-2-ene (Reference should be made to the article by the inventors published in J. Org. Chem., 40, 276 (1975)) at its position 4 substituted with chlorine, and subjecting the obtained product successively to dechlorination and hydrogen addition methods.

The compound (VI) may be, for instance, synthesized by reducing 6,7-exo-trimethylenebicyclo[3.2.1]oct-3-ene (Reference should be made to the article by the inventors published in J. Org. Chem., 40, 276 (1975)) with the use of lithium aluminum hydride.

The compound (VII) may have either exo- or endo-hydroxyl group at position 2 thereof, and either one of which gives the desired compound (I) at the selectivity coefficient of 90% or more. The 2-exo-hydroxy epimer of the compound (VII), i.e. 2-exo-hydroxy-5,6-endo-trimethylenebicyclo[2.2.2]octane (hereinbelow referred to as (VIIx)), may be synthesized by the hydroboration of endo-tricyclo[5.2.2.0$^{2,6}$]undeca-8-ene (IX) as shown in the following reaction formula; and the 2-endo-hydroxy epimer of the compound (VII), i.e. 2-endo-hydroxy-5,6-endotrimethylenebicyclo[2.2.2]octane (hereinbelow referred to as (VIIn)), may be synthesized by reducing endo-tricyclo[5.2.2.0$^{2,6}$]undeca-8-ene (X), which is obtained by Jones' oxidation of the compound (VIIx), with the use of lithium aluminum hydride.

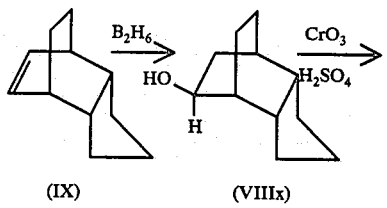

(IX) (VIIIx)

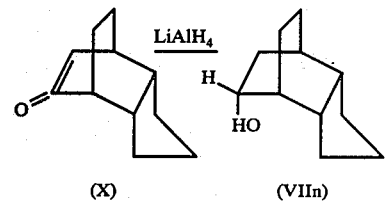

(X) (VIIn)

The compound (VIII) is also a novel tricycloundecane and may be synthesized, for example, by dechlorinating 3,4-dichloro-6,7-exo-trimethylenebicyclo[3.2.1]-octo-2-ene with the use of sodium and liquid ammonia.

The structure of the thus-obtained compound of the formula (I) can be confirmed by the fact that tricyclo[6.2.1.0$^{2,6}$]undecane (III) obtained by hydrogenation of the thus-obtained formula (I) compound is in agreement with the standard substance (III) prepared according to the following scheme:

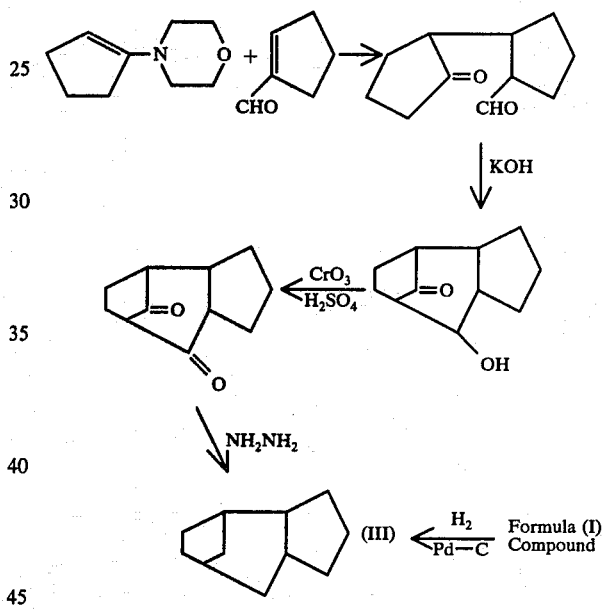

REFERENCE EXAMPLE

A mixture containing 0.21 g (0.0014 mols) of the compound (I) having a purity of 88.6%, 0.06 g of a palladium (5%)-carbon catalyst and 8 ml of ethyl acetate was put into an autoclave and the compound was subjected to hydrogen addition reaction at 120° C for 18 hours in the presence of hydrogen under a hydrogen pressure of 50 kg/cm$^2$.

Ethyl acetate was distilled off and the obtained residue was analysed using Colen's column gas chromatography mass spectrometry. The retention time and mass spectrum of the main product (51.6% of the residue) was coincident with those of the standard sample of tricyclo[6.2.1.0$^{2,6}$]undecane (III).

An example of the present invention will now be described together with a preparation illustrating the synthesis of the starting formula (I) compound.

PREPARATION 1

A mixture of 10 g of 2-hydroxymethyl-5,6-exo-trimethylenenorbornane (IV), 300 g of 85% phosphoric acid and 500 ml of n-heptane was heated and refluxed for 7 hours with stirring. The heptane layer was separated, washed with water, dried with calcium chloride and analyzed by gas chromatography and mass spectrometry. It was found that the reaction product comprised 11.5% of 6,7-exo-trimethylenebicyclo[3.2.1]oct-2-ene, 71.8% of tricyclo[6.2.1.0$^{2,6}$]undeca-2(6)-ene (I) and 16.7% of several compounds having an unknown structure.

By preparative gas chromatography of the above mixture, the formula (I) compound having a purity of 88.6% was obtained.

IR Spectrum (liquid film), cm$^{-1}$: 3050 (shoulder), 2940, 2860, 1660 (weak), 1450, 1290, 1050, 940

$^1$H NMR (CDCl$_3$, δ): 0.8 – 3.0 (m)

$^{13}$C NMR (CDCl$_3$, ppm): 22.54 (t, 1), 30.74 (t, 1), 33.75 (d, 1), 34.60 (t, 2), 35.37 (t, 1), 36.30 (d, 1), 36.71 (t, 1), 37.12 (t, 1), 130.11 (s, 1), 142.29 (s, 1)

Elementary Analysis Values as C$_{11}$H$_{16}$: Calculated: C, 89.1%; H, 10.9%. Found: C, 88.9%; H, 11.0%.

The thus-separated product was analyzed by Golay column gas chromatography and mass spectrometry, and the following mass spectrum of the pure product (I) was obtained:

m/e (relative intensity): 148 (35, M$^+$), 120 (23), 119 (100), 105 (14), 92 (18), 91 (72), 80 (15), 79 (33), 77 (16), 66 (14), 53 (8), 51 (8), 41 (20), 39 (19)

PREPARATION 2

A mixture containing 1.0 g of 2-hydroxy-6,7-exo-trimethylenebicyclo[3.2.1]octane (V), 30 g of 85% phosphoric acid and 50 ml of n-heptane was subjected to reflux at about 100° C for 17 minutes under agitation. The n-heptane layer was separated, washed with water and dried with anhydrous calcium chloride. Then, n-heptane was distilled off and 0.58 g of a mixture composed of 51.5% of the compound (I), 33.2% of 6,7-exo-trimethylenebicyclo[3.2.1]oct-2-ene, which is novel, and 15.3% of the other compounds was obtained (Yield: 64%).

The compound (I) having a purity of 88.6% was obtained by separating through a fractional chromatography.

IR (Liquid film): 3050 (shoulder), 2940, 2860, 1660 (feeble), 1450, 1290, 1050, 940 cm$^{-1}$ $^1$HNMR (CDCl$_3$, δ): 0.8 – 3.0 (m)

$^{13}$CNMR (ppm (Triplet, relative strength)): 22.54 (t, 1), 30.74 (t, 1), 33.75 (d, 1), 34.60 (t, 2), 35.37 (t, 1), 36.30 (d, 1), 36.71 (t, 1), 37.12 (t, 1), 130.11 (s, 1), 142.29 (s, 1)

Ultimate Analysis: As C$_{11}$H$_{16}$: Cald.: C, 89.1; H, 10.9%. Found: C, 88.9; H, 11.0%.

The above sample was analysed using Goley's column gas chromatography mass spectrometry to measure the mass spectrum of the compound (I). The measured m/e (relative strength) are as follows:

148 (35, M$^+$), 120 (23), 119 (100), 105 (14), 92 (18), 91 (72), 80 (15), 79 (33), 77 (16), 66 (14), 53 (8), 51 (80), 41 (20), 39 (19)

PREPARATION 3

A mixture containing 1.0 g of 3-endo-hydroxy-6,6-exo-trimethylenebicyclo[3.2.1]octane (VI), 30 g of 85% phosphoric acid and 50 ml of n-heptane was subjected to reflux at about 100° C for 45 minutes under agitation. The n-heptane layer was separated, washed with water and dried with anhydrous calcium chloride. Then, n-heptane was distilled off and 0.55 g of a mixture composed of 46.1% of the compound (I), 28.0% of 6,7-exo-trimethylenebicyclo[3.2.1]oct-2-ene and 25.9% of the other compounds was obtained (Yield: 61%).

The compound (I) having a purity of 88.6% was obtained by separating through fractional chromatography.

IR (Liquid film) 3050 (shoulder), 2940, 2860, 1660 (feeble), 1450, 1290, 1050, 940 cm$^{-1}$ HNMR (CDCl$_3$, δ) 1.8 – 3.0 (m)

$^{13}$CNMR (ppm (multiplet, relative strength)) 22.54 (t, 1), 30.74 (t, 1), 33.75 (d, 1), 34.60 (t, 2), 35.37 (t, 1), 36.30 (d, 1), 36.71 (t, 1), 37.12 (t, 1), 130.11 (s, 1), 142.29 (s, 1)

Ultimate Analysis: As C$_{11}$H$_{16}$: Cald.: C, 89.1; H, 10.9%. Found: C, 88.9; H, 11.0%.

The above sample was analysed using Goley's column gas chromatography mass spectrometry to measure the mass spectrum of the compound (I). The measured m/e (relative strength) are as follows:

148 (35, M$^+$), 120 (23), 119 (100), 105 (14), 92 (18), 91 (72), 80 (15), 79 (33), 77 (16), 66 (14), 53 (8), 51 (8), 41 (20), 39 (19)

PREPARATION 4

A mixture composed of 1.0 g of 2-exo-hydroxy-5,6-endo-trimethylenebicyclo[2.2.2]octane, 30 g of 85% phosphoric acid and 50 ml of n-heptane was subjected to reflux at about 100° C for 25 minutes under agitation. The n-heptane layer was separated, washed with water and dried with anhydrous calcium chloride. Then, n-heptane was distilled off and 0.72 g of a mixture composed of 45.5% of the compound (I), 30.6% of 6,7-exo-trimethylenebicyclo[3.2.1]oct-2-ene and 23.9% of the other compounds was obtained (Yield: 80%).

IR (Liquid film): 3051 (shoulder), 2940, 2860, 1660 (feeble), 1450, 1290, 1050, 940 cm$^{-1}$ HNMR (CDCl$_3$, δ): 0.8 – 3.0 (m)

$^{13}$CNMR (ppm (multiplet, relative strength)) 22.54 (t, 1), 30.74 (t, 1), 33.75 (d, 1) 34.60 (t, 2), 35.37 (t, 1), 36.30 (d, 1) 36.71 (t, 1), 37.12 (t, 1), 130.11 (s, 1), 142.29 (s, 1)

Ultimate Analysis: As C$_{11}$H$_{16}$: Cald.: C, 89.1; H, 10.9%. Found: C, 88.9; H, 11.0%.

The above sample was analysed using Goley's column gas chromatography mass spectrometry to determine the mass spectrum of the compound (I). The measured m/e (relative strength) are as follows:

148 (35, M$^+$), 120 (23), 119 (100), 105 (14), 91 (72), 80 (15), 79 (33), 77 (16), 66 (14), 53 (8), 51 (8), 41 (20), 39 (19).

PREPARATION 5

Following the general procedure in Preparation 4, 1.0 g of 1,2-endo-hydroxy-5,6-endo-trimethylenebicyclo[2.2.2]octane was subjected to reflux for 10 minutes. The reaction mixture was treated similarly as in Preparation 4, and 0.79 g of a mixture composed of 68.8% of the compound (I), 22.9% 6,7-exo-trimethylenebicyclo[3.2.1]oct-2-ene and 8.3% of the other compounds was obtained (Yield: 87%).

The results of IR, HNMR and MS (mass spectrometry) analyses of the compound (I) having a purity of 88.6% which was obtained by separating through fractional gas chromatography were consistent with the results of the compounds (I) obtained in Preparation 4.

PREPARATION 6

A mixture containing 1.0 g of 6,7-exo-trimethylenebicyclo[3.2.1]oct-2-ene (VIII), 30 g of 85% phosphoric acid and 50 ml of n-heptane was subjected to reflux at about 100° C for 10 minutes under agitation.

The n-heptane layer was separated, washed with water and dried with anhydrous calcium chloride. After then, n-heptane was distilled off and 0.83 g of a mixture composed of 85.0% of the compound (I), 0.6% of the unreacted compound (VIII) and 14.4% of the other compounds was obtained (Yield: 83%).

The compound (I) having a purity of 88.6% was obtained by separating through fractional chromatography.

IR (Liquid film): 3050 (shoulder), 2940, 2860, 1660 (feeble), 1450, 1290, 1050, 940 cm$^{-1}$ $^1$HNMR (CDCl$_3$, δ): 0.8 – 3.0 (m)

$^{13}$CNMR (ppm (multiplet, relative strength)) 22.54 (t, 1), 30.74 (t, 1), 33.75 (d, 1), 34.60 (t, 1), 35.37 (t, 1), 36.30 (d, 1), 36.71 (t, 1), 37.12 (t, 1), 130.11 (s, 1), 142.29 (s, 1)

Ultimate Analysis: As C$_{11}$H$_{16}$: Cald.: C, 89.1; H, 10.9%. Found: C, 88.9; H, 11.0%.

The above sample was analysed using Goley's column gas chromatography mass spectrometry to measure the mass spectrum of the compound (I). The measured m/e (relative strength) are as follows:

148 (35, M$^+$), 120 (23), 119 (100), 105 (14), 92 (18), 91 (72), 80 (15), 79 (33), 77 (16), 66 (14), 53 (8), 51 (8), 41 (20), 39 (19)

EXAMPLE 1

A mixture of 1.0 g of tricyclo[6.2.1.0$^{2,6}$]undeca-2(6)-ene obtained in the preparation, 10 g of 95% sulfuric acid and 50 ml of n-pentane was vigorously agitated at room temperature for 10 minutes. The reaction mixture was then allowed to stand still, and the separated n-pentane layer was collected, washed with water and dried with calcium chloride. Distillation of n-pentane gave 0.36 g (the yield being 36%) of a crude product as the solid residue. When the crude product was analyzed by gas chromatography and mass spectrometry, it was found that the crude product contained 91.8% of 4-homoisotwistane (II).

When the crude product was sublimed under reduced pressure, 0.30 g (the yield being 33%) of a pure product of the formula (II) compound was obtained. Results of the measurement of the melting point, the IR spectrum, the $^1$H NMR analysis and the mass spectrum analysis were in agreement with those of the authentic specimen. [Refer to our report, J. Org. Chem., 40, 276 (1975)].

The embodiments of the invention in which an exclusive property or privilege is claimed are defined as follows:

1. Tricyclo[6.2.1.0$^{2,6}$]undeca-2(6)-ene.
2. A process for preparing tricyclo[6.2.1.0$^{2,6}$]undeca-2(6)-ene, which comprises, contacting 5,6-exo-trimethylene-2-norbornylcarbinol with phosphoric acid having a concentration of from 50 to 100%, at a temperature in the range of from 50° to 150° C, to effect dehydration isomerization of said 5,6-exo-trimethylene-2-norbornylcarbinol to transform same to tricyclo[6.2.1.0$^{2,6}$]undeca-2(6)-ene.

* * * * *